(12) United States Patent
Potas et al.

(10) Patent No.: US 9,448,213 B2
(45) Date of Patent: Sep. 20, 2016

(54) RESIDUAL STERILANT TEST METHOD

(71) Applicant: Saban Ventures Pty Limited, Lane Cove, New South Wales (AU)

(72) Inventors: Michael Potas, Earlwood (AU); Vladimir Berentsveig, Redfern (AU)

(73) Assignee: Saban Ventures Pty Limited, Lane Cove, New South Wales (AU)

( * ) Notice: Subject to any disclaimer, the term of this patent is extended or adjusted under 35 U.S.C. 154(b) by 0 days.

(21) Appl. No.: 14/891,163

(22) PCT Filed: May 12, 2014

(86) PCT No.: PCT/AU2014/000512
§ 371 (c)(1),
(2) Date: Nov. 13, 2015

(87) PCT Pub. No.: WO2014/183155
PCT Pub. Date: Nov. 20, 2014

(65) Prior Publication Data
US 2016/0116449 A1 Apr. 28, 2016

(30) Foreign Application Priority Data

May 13, 2013 (AU) ................. 2013901675

(51) Int. Cl.
| | | |
|---|---|---|
| *A61L 2/20* | (2006.01) | |
| *G01N 21/78* | (2006.01) | |
| *G01N 31/22* | (2006.01) | |
| *A61L 2/18* | (2006.01) | |
| *A61L 2/22* | (2006.01) | |
| *A61L 2/26* | (2006.01) | |

(52) U.S. Cl.
CPC ............. *G01N 31/226* (2013.01); *A61L 2/186* (2013.01); *A61L 2/208* (2013.01); *A61L 2/22* (2013.01); *A61L 2/26* (2013.01); *G01N 21/78* (2013.01); *A61L 2202/24* (2013.01)

(58) Field of Classification Search
CPC ...... G01N 21/25; G01N 21/29; G01N 21/78; G01N 31/00; G01N 31/22; G01N 31/226; G01N 31/228; Y10T 436/15; Y10T 436/156666; Y10T 436/19; Y10T 436/206664; Y10T 436/25; Y10T 436/25125; Y10T 436/25875; A61L 2202/24; A61L 2/186; A61L 2/208; A61L 2/22; A61L 2/26
USPC ........... 436/1, 100, 102, 119, 124, 135, 163, 436/164, 166, 174, 175, 181; 422/1, 28, 30
See application file for complete search history.

(56) References Cited

U.S. PATENT DOCUMENTS

| | | | | |
|---|---|---|---|---|
| 6,333,002 B1* | 12/2001 | Jacobs | .................... | A61L 2/208 422/3 |
| 6,365,102 B1* | 4/2002 | Wu | .......................... | A61L 2/14 422/23 |
| 2003/0219389 A1* | 11/2003 | Sagel | .................. | A61K 8/0208 424/53 |
| 2005/0019206 A1 | 1/2005 | Centanni | | |
| 2008/0219884 A1* | 9/2008 | Berentsveig | ........... | A01N 25/06 422/33 |

FOREIGN PATENT DOCUMENTS

EP 1459771 A2 9/2004

OTHER PUBLICATIONS

International Search Report issued Jul. 1, 2014, in PCT/AU2014/000512, 4 pages.

* cited by examiner

*Primary Examiner* — Maureen Wallenhorst
(74) *Attorney, Agent, or Firm* — Senniger Powers LLP

(57) ABSTRACT

Methods for determining the amount of residual sterilant remaining on the surface of an object at the end of a disinfection process are described. One method of determining the amount of residual sterilant on a test piece after a sterilization regime in a sterilization space includes the steps of: placing a test piece having a predetermined surface area into the sterilization space; subjecting the test piece to the sterilization regime; collecting the residual sterilant from the test piece in a collector solution; and measuring the amount of residual sterilant in the collector solution.

22 Claims, No Drawings

RESIDUAL STERILANT TEST METHOD

REFERENCE TO CORRESPONDING APPLICATIONS

The present application is the 371 national stage application based on International Application No. PCT/AU2014/000512, filed May 12, 2014, which claims priority to Australian Patent Application No. 2013901675, filed May 13, 2013, the entire contents of which are incorporated herein by reference.

FIELD OF THE INVENTION

The present invention relates to methods for determining the amount of residual sterilant remaining on the surface of an object at the end of a disinfection process.

BACKGROUND

"Sterilization" has been defined as the process of destroying all microorganisms, spores and their pathogenic products. A 6 log reduction in the amount of such pathogens is generally required to provide a suitable sterility assurance level. "Disinfection" is a similar process, the difference being that it results in a lesser degree of biocidal effect, particularly on bacterial spores. Disinfection is thus easier to achieve than sterilization.

The term "sterilant" will be used throughout although it is understood to encompass both "sterilant" and "disinfectant".

Heat has traditionally been one option for carrying out sterilization. However, heat sterilization is not always practical, for example, when sterilizing heat-sensitive articles, such as certain medical instruments, or when sterilizing large areas, as in the case of room sterilization. For this reason, low-temperature sterilization is often the best option.

Low-temperature sterilants are usually liquids and can be applied to articles requiring disinfection or sterilization in a variety of ways. In recent years, the use gas or aerosol dispensing technologies to dispense sterilants has become widespread. Gas or aerosol processes are particularly attractive since they reduce the amount of liquid sterilant used. The primary benefit of using micro volumes of liquid is that rinsing steps can sometimes be eliminated and drying times are often significantly reduced compared to using say, soaking baths. This shortened cycle time reduces the turnaround time for any given instrument which in turn translates into a much smaller capital outlay tied up in instruments.

Gas or aerosol processes also tend to be conducted in closed systems, which means that operator safety is also enhanced relative to conventional methods that expose workers to large volumes of open sterilant solutions.

In recent years the use of hydrogen peroxide or peracetic acid as a sterilant has become greatly preferred. Hydrogen peroxide has been used in the vapour phase for disinfection or sterilization. Vapour phase systems generally employ small volume chambers such as sterilizers that can be evacuated since the vapours are more effective at very low pressures or as plasmas. At the end of the treatment cycle, residual hydrogen peroxide vapour is pumped out by a vacuum pump and exhausted to the atmosphere directly or via a catalytic destroyer which decomposes any residual peroxide vapour into harmless oxygen and water.

Peroxide vapours have also been used at atmospheric pressure but in that case longer treatment times are generally involved than in vacuum systems and efficacy against bacterial spores has been shown to be limited. After treatment in small scale peroxide vapour systems, air is circulated through the chamber and any residual peroxide is either flushed directly into the atmosphere through a HEPA-filter, or is flushed into the atmosphere via a catalytic destructor so that the peroxide is catalysed to oxygen and water prior to disposal. In some recirculating systems the flow may be diverted after the treatment and recirculated by an air pump though a catalytic destroyer placed in parallel with the treatment circuit until peroxide is eliminated.

Others have endeavoured to use peroxide aerosols (rather than vapour) as the biocidal agent for sterilization or disinfection of small chambers. Aerosols have a number of major advantages over vapour process. A much higher concentration density of active species is obtainable at atmospheric pressure for aerosols than for vapours. Aerosols also eliminate the need for costly vacuum equipment. In some such cases the aerosol flow may be diverted through a catalytic destructor after the treatment cycle is completed to remove any peroxide residues.

While such stable aerosols of aqueous biocides, preferably hydrogen peroxide, can be employed at atmospheric pressure and above which avoid the need for vacuum equipment, elimination of residual hydrogen peroxide on the surface of sterilized articles nevertheless remains a significant problem.

In the food sterilization field, even trace amounts of hydrogen peroxide can affect the flavour or colour of the product. Food packaging regulations now limit hydrogen peroxide residues on containers to a maximum of 0.5 ppm in the United States.

In the case of medical instruments, even a small amount of residual peroxide on an ultrasound probe or similar could have potentially serious consequences for a patient if the probe were to be placed in direct contact with the patient's skin or mucosa. Peroxide in high concentrations is highly corrosive and can result in severe wounding. For similar reasons, the use of peroxide as a sterilant means that occupational health and safety measures need to be in place to ensure the safety of staff working in disinfected environments.

Surface residues of peroxides in operating theaters or on surgical instruments should be below 100 mkg/cm$^2$. To achieve such levels by blowing or sucking air even though small chamber volumes for sterilizing instruments or the like can add significantly to process times, especially when the incoming air needs also to be HEPA-filtered to maintain sterility. The removal step thus adds greatly to treatment times because the residual balance of peroxide reduces asymptotically. The larger the volume of space treated the more difficult the removal problem becomes.

Similar considerations apply to biocides other than peroxides.

In addition, it is not feasible to check every sterilization cycle of every apparatus or every room or space treated in order to ensure complete sterilization. Certification of sterilant removal, i.e. guaranteed removal of the sterilant or reduction of the sterilant to a certain level is highly desirable. Following the stated protocol as a way to achieve a guaranteed or certified outcome is very efficient mode of operation. However, it can still be highly desirable to perform a quick test to confirm experimentally whether a guaranteed level of certification of sterilant removal is actually achieved. Ideally, such a test would be "on/off" or 'go/no-go", meaning that the when the test is conducted, a clear answer would be given as to whether a certain level of residual was present or not.

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

SUMMARY OF THE INVENTION

In a broad first aspect the invention provides a method of determining the amount of residual sterilant on a test piece after a sterilization regime in a sterilization space, the method comprising the steps of:

placing a test piece having a predetermined surface area into the sterilization space;

subjecting the test piece to the sterilization regime;

collecting the residual sterilant from the test piece in a collector solution; and measuring the amount of residual sterilant in the collector solution.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The sterilization space can in one embodiment the sterilization chamber of a sterilization apparatus. In another embodiment, the sterilization space can be a larger space or room which is being disinfected.

In a particularly preferred aspect, the invention provides a method of determining whether the amount of residual sterilant on a test piece after a sterilization regime in a sterilization space exceeds a predetermined threshold.

In one embodiment, the step of collecting the residual sterilant from the test piece in a collector solution is performed by placing the test piece into a collector solution. In another embodiment, the step of collecting the residual sterilant from the test piece in a collector solution is performed by washing the test piece with a collector solution Preferably, the collector solution is used in a predetermined amount.

In one embodiment, the step of measuring the amount of residual sterilant in the collector solution is by direct measurement of the sterilant.

In another embodiment the step of measuring the amount of residual sterilant in the collector solution is by indirect measurement of the sterilant.

According to second aspect the invention provides a method of determining whether the amount of residual sterilant on a test piece after a sterilization regime in a sterilization space exceeds a predetermined threshold; the method comprising the steps of:

placing a test piece having a predetermined surface area into a sterilization space;

subjecting the test piece to the sterilization regime;

placing the test piece into a first solution containing a known amount of a first species reactive with the sterilant;

adding to the first solution a known amount of a second species reactive with the first species, whereby the first species and second species are reactive to provide a result having a first visual appearance if the amount of residual sterilant is above a predetermined level or having a second visual appearance if the amount of residual sterilant is below a predetermined level; and wherein the first visual appearance and second visual appearance are non-identical.

In an alternative embodiment, the first species is reactive with the sterilant to provide a result wherein the an appearance can be correlated with the amount of residual sterilant.

In another alternative embodiment, the first solution and sterilant are reactive and the first solution and second solution are reactive to provide a result wherein the an appearance can be correlated with the amount of residual sterilant.

In a preferred embodiment, the sterilant is hydrogen peroxide.

For preference, the test piece is peroxide resistant plastic or glass. It may have any shape, but ideally the shape is simple The predetermined threshold would be any regulatory or practical level of residual sterilant that was the minimum amount considered to be harmful to humans. Typically, such residual thresholds are expressed in terms of mass per unit area, (e.g., $\mu g/cm^2$).

In one embodiment, the sterilization regime comprises contacting the test piece with an aerosol of hydrogen peroxide in a sterilization space followed by removal of the aerosol from the sterilization space. Most preferably, the sterilization regime comprises contacting the test piece with an aerosol of hydrogen peroxide in a sterilization space followed by removal of the aerosol from the sterilization space.

Preferably the first solution contains sulfuric acid and iodide. The first solution is preferably prepared immediately prior to use by mixing a precursor solution comprising sulfuric acid with a precursor solution comprising iodide.

Preferably the first species reactive with the sterilant is iodide. Preferably the second species reactive with the first species is thiosulfate.

Preferably the first species and second species when mixed are monitored for a visual appearance at a predetermined time after mixing, for example 5 seconds.

Preferably the first visual appearance if the amount of residual sterilant is above a predetermined level is a yellow or brown color. Preferably the first visual appearance is caused by the presence of $I_2$ or $I_3^-$.

Preferably the second visual appearance if the amount of residual sterilant is below a predetermined level is a colorless appearance.

DETAILED DESCRIPTION

The method of the present invention enables a measurement of the amount of residual sterilant on a test piece after a sterilization regime in a sterilization space. It can be used to quantify the amount of sterilant or to determine whether the amount of residual sterilant meets or exceeds a predetermined threshold value.

The method involves placing a test piece having a predetermined surface area into the sterilization space or subjecting the test piece to the usual sterilization regime, removing the test piece from the sterilization space and collecting the residual sterilant from the test piece by way of a collector solution. In one embodiment, for example, a test piece of known area is placed in a chemical sterilizer (which may be bulk liquid, vapour or aerosol) and sterilized under the normal operating conditions (including time, concentration, temperature, aerosol removal and cycling) for that space that would be considered sufficient to certify sterilization.

The test piece is desirably of simple construction, such as a small strip or square that can easily be supported in the space. The test strip could be made of a one or more materials, including but not limited to plastics and metals that are commonly sterilized.

Once the sterilization process is finished, the test piece is removed carefully so as not to disturb any residual sterilant, but also as quickly as practicable so as not to allow for evaporation of sterilant peroxide which could provide a false negative.

The most preferred approach for collecting the residual sterilant is for the test piece simply to be immersed in the collector solution. Ideally, it is not removed from the collector solution for the remainder of the test. Alternatively however, the test piece can be rinsed with a collector solution and the total rinse volume collected.

The collector solution is preferably used in a predetermined amount, so that the concentration of the sterilant collected can be determined.

The step of measuring the amount of residual sterilant in the collector solution can be by direct or indirect means. The choice of direct or indirect measurement will depend upon the nature of the sterilant.

For example, direct measurement may be applicable for a sterilant that is UV active (having an aromatic ring or forming a charge transfer complex, for instance) directly subjecting the collector solution or a treated collector solution to UV spectroscopy. The use of a calibration curve will enable the concentration of the residual sterilant in the collector solution to be determined. Because the volume of collector solution is known, the total amount of sterilant can thus be determined. Because the area of the test piece is known, a figure for the amount of sterilant per unit area can be determined.

Any species which can have its concentration determined spectroscopically can have the amount of residual sterilant measured in this way.

Direct measurement may also be possible if the sterilant can be analysed via titration (for instance, in the case of acidic or basic sterilants) where an endpoint can be used to determine the concentration of sterilant present in the collector solution.

For species which are difficult to quantify directly, indirect measurement of the sterilant may be possible. An example of indirect measurement would be in the case of a sterilant reacting stoichiometrically with an agent that was quantifiable.

An important sterilant which is difficult to quantify by direct measurement is hydrogen peroxide. It is preferred if peroxide can be determined indirectly, via its stoichiometric reaction with iodide, and subsequent titration with a reductant. The following nonlimiting explanation is provided by way of example.

The present invention in a particular embodiment relates to a test to determine whether the amount of a sterilant, particularly hydrogen peroxide on a surface is above or below a certain predetermined threshold level. The test may be used for example to determine the level of peroxide residue (in terms of mass/unit area) left on a sterilized article at the completion of the sterilization process.

In principle, a test piece of known area is placed in a chemical sterilizer (which may be bulk liquid, vapour or aerosol) and sterilized under the normal operating conditions (including time, concentration, temperature, aerosol removal and cycling) for that space that would be considered sufficient to certify sterilization.

The test piece is desirably of simple construction, such as a small strip or square that can easily be supported in the space. The main thing is that the test piece is of precisely known surface area. The test strip could be made of a one or more materials, including but not limited to plastics and metals that are commonly sterilized.

Once the sterilization process is finished, the test piece is removed carefully so as not to disturb any deposited peroxide, but also as quickly as practicable so as not to allow for evaporation of peroxide which could provide a false negative.

The test piece is then subject to the following:

An aqueous solution of sulfuric acid and iodide is prepared immediately before use by mixing sulfuric acid with a sodium iodide solution in a suitable container. The test strip is then placed into this solution and a further solution containing thiosulfate is then added. The whole container, including the test strip in the liquid is then shaken for about 5 seconds. It is important that any loss of liquid is minimised during the mixing and shaking procedure.

The quantities of each component are decided beforehand depending upon the desired threshold level that is chosen. The chemistry and method of calculation will be illustrated below for the example.

If the amount of residual peroxide per unit area on the test strip exceeds the calculated threshold, then the solution will turn yellow. If the solution does not turn yellow, the level of peroxide per unit area on the test strip does not exceed the calculated value.

To explain further, the chemistry of the present invention involves the following two reactions:

$$H_2O_2 + 2NaI + H_2SO_4 \rightarrow I_2 + NaSO_4 + 2H_2O$$

and then $$I_2 + 2Na_2S_2O_3 \rightarrow Na_2S_4O_6 + 2NaI$$

In this system, water, sodium iodide and sulfuric acid are provided in comfortable excess. However, other alkali metal iodides, for example, potassium iodide, may be used as an alternative source of iodide to sodium iodide. The amount of iodine produced will be in an equimolar to the amount of peroxide present, which is the variable being measured. The amount of iodine thus produced acts as a visible proxy for the amount of peroxide present on the test piece.

Thus, it can be seen that if the molar amount of peroxide: thiosulfate equals 1:2 (and consequently, the ratio of iodine: thiosulfate is 1:2), then the reaction will be balanced, and the net amount of iodine produced will be zero, since the two equations will cancel each other out.

If the molar ratio of peroxide:thiosulfate is less than 1:2 ratio (and consequently, the ratio of iodine:thiosulfate is less than 1:2), then there will be excess thiosulfate, meaning that all iodine will be consumed, and reduced to I$^-$.

However, if the molar ratio of peroxide:thiosulfate exceeds a 1:2 ratio (and consequently, the ratio of iodine: thiosulfate exceeds 1:2), then there will be a deficit of thiosulfate to reduce the iodine. Some, but not all, of the iodine will be reduced to I$^-$. There will thus be an excess of iodine, which will present a visible colour (the visible colour is actually caused by iodine and iodide forming soluble, I$_3^-$ which is brown at high concentrations and yellow at lower concentrations).

The above chemistry can be exploited in a manner which can test for a predetermined molar amount of peroxide.

In the present case, the test is to determine whether the amount of peroxide in grams per unit area on the test piece falls above a certain amount. The molecular weight of peroxide is known, as is area A of the test piece, so it becomes only necessary to determine whether the total molar amount of peroxide is at Q moles or above. The amount of sulfuric acid and alkali metal iodide (for example, sodium iodide or potassium iodide) are chosen to be comfortably in excess of Q, but an exact quantity of 2Q moles of thiosulfate is required when testing for a total of Q moles of peroxide residue. If more than Q moles of peroxide are present, the test will show a positive colour for iodine. If Q or less than Q moles of peroxide are present, the test will not show any iodine colour.

EXAMPLE

The following example illustrates the present invention:

Health regulations vary from jurisdiction to jurisdiction and application to application as to the level of residual hydrogen peroxide on the surface of a sterilized article following sterilization that would be considered safe. For the following purposes, we will define the safe concentration as 250 ng per square centimeter of article.

In the present example, a test piece, being a strip of smooth plastic, of area 10 cm$^2$ is placed in the sterilizer and is subjected to the sterilizer's standard sterilization regime.

Whilst the sterilizer is completing its process, the following two solutions are mixed in a separate container:
  Precursor solution A containing 1M sulfuric acid, 20 mL.
  Precursor solution B containing 10% sodium iodide or potassium iodide Solution, 3 mL.

The solutions A and B are provided in unmixed two part form for maximum accuracy. The solutions should be mixed just prior to their intended use, since the quantity of free iodine can reduce over long term storage.

Once the standard sterilization regime is complete, the test piece is removed from the sterilizer and introduced into the container containing the mixed precursor A and B solutions.

To this mixture, the following solution is then added as soon as practicable:
  Solution C containing 0.05N sodium thiosulfate solution, 3 mL The container, including the test strip, is then shaken for 5 seconds. It is desirable if the containers are closed, since loss of liquid during shaking can result in errors.

If the solution remains clear/colourless, the residual peroxide on the test carrier is at or below the predetermined threshold limit, in this case 250 µg/cm$^2$.

If the solution turns a yellow colour, the residual peroxide on the test carrier was above the 250 µg/cm$^2$ threshold limit.

The above concentrations are specifically formulated to determine whether there is more or less than 250 µg/cm$^2$ over a 10 cm$^2$ surface, but these can be adapted to different surface areas and levels of residue.

250 µg/cm$^2$ of hydrogen peroxide on a 10 cm$^2$ surface equates to a total mass of 2520 µg of hydrogen peroxide. Hydrogen peroxide has a molecular mass of 34 g/mol, so the threshold test is in effect looking to determine whether the test strip carries in excess of $7.4 \times 10^{-5}$ moles of hydrogen peroxide.

The amount of I$^-$ used is around 0.002 moles, comfortably in excess of the peroxide level being tested. The amount of sulfuric acid is also in comfortable excess.

However, the amount of thiosulfate is carefully chosen to give a stoichiometric reaction with the iodine produced—in this case 0.00015 moles (twice the molar amount of peroxide threshold being tested, which is the exact stoichiometric ratio to give the desired result).

These calculations could be readily modified to adjust for the changes in the predetermined threshold value and/or test strip area.

In addition, the current test is highly sensitive. The visual detection limit of (I$_2$/I$^-$) systems (I$_3^-$) has been estimated to be of the order of $5 \times 10^{-6}$M. The exemplified solution has $7.4 \times 10^{-5}$ moles in 26 mL total volume, which translates to a molarity of 0.0028M. Thus, the relative precision of this test ($5 \times 10^{-6}$ in $3 \times 10^{-3}$) is extremely high.

The counter ions and acid can be varied, substituting equivalents as necessary or desired.

This method can thus allow ready onsite re-validation of certified residual amounts of peroxide, in a "go/no-go" fashion.

Alternatively, this method can also provide a quick test for certification of an instrument prior to release for sale.

The test can also be worked in a semi-quantitative manner in which a number of test pieces are removed from the sterilizer and placed into a graded series of solutions prepared with different quantities of thiosulfate intended to capture different peroxide residues. Alternatively, a suite of differently sized test pieces could be used in a number of parallel tests. In this way, a wider range of peroxide residues could be evaluated, each discrete point giving a "go/no-go" result.

The present invention, using a test strip and a small number of solutions, is highly portable and very suitable for end user on-site testing. This invention allows for an accurate test to be conducted relatively inexpensively and can be carried out by following simple instructions, with no training required.

The claims defining the invention are as follow:

1. A method of determining an amount of residual sterilant on a surface area of a test piece after a sterilization regime in a sterilization space, the method comprising:
  placing the test piece into the sterilization space;
  subjecting the test piece to the sterilization regime;
  removing the test piece from the sterilization regime or stopping the sterilization regime;
  collecting the residual sterilant from the surface area of the test piece in a collector solution; and
  measuring the amount of residual sterilant in the collector solution,
  wherein the surface area of the test piece is predetermined.

2. A method according to claim 1 wherein the sterilization space is a sterilization chamber or a room.

3. A method according to claim 1 wherein the sterilization regime comprises contacting the test piece with an aerosol of hydrogen peroxide in the sterilization space followed by removing the aerosol from the sterilization space.

4. A method according to claim 1 further comprising determining whether the amount of residual sterilant on the test piece after the sterilization regime in the sterilization space exceeds a predetermined threshold.

5. A method according to claim 1 wherein collecting the residual sterilant from the test piece in the collector solution is performed by placing the test piece into the collector solution or by washing the test piece with the collector solution.

6. A method according to claim 4 wherein collecting the residual sterilant from the test piece in the collector solution is performed by placing the test piece into the collector solution or by washing the test piece with the collector solution.

7. A method according to claim 1 wherein the collector solution is used in a predetermined amount.

8. A method according to claim 1 wherein measuring the amount of residual sterilant in the collector solution is by direct or indirect measurement of the sterilant.

9. A method according to claim 1 wherein the method comprises removing the test piece from the sterilization regime.

10. A method of determining whether an amount of residual sterilant on a surface area of a test piece after a sterilization regime in a sterilization space exceeds a predetermined threshold, the method comprising:
    placing the test piece into the sterilization space;
    subjecting the test piece to the sterilization regime;
    removing the test piece from the sterilization regime or stopping the sterilization regime;
    placing the test piece into a first solution containing a known amount of a first species reactive with the sterilant present on the surface area of the test piece; and
    adding to the first solution a known amount of a second species reactive with the first species,
    wherein the surface area of the test piece is predetermined,
    wherein the first species and second species are reactive to provide a result having a first visual appearance if the amount of residual sterilant exceeds the predetermined threshold or having a second visual appearance if the amount of residual sterilant is below the predetermined threshold; and wherein the first visual appearance and second visual appearance are non-identical.

11. A method according to claim 10 wherein the sterilization space is a sterilization chamber.

12. A method according to claim 10 wherein the sterilant comprises hydrogen peroxide and the test piece comprises peroxide resistant plastic or glass.

13. A method according to claim 12 wherein the first species reactive with the sterilant is iodide and/or the second species reactive with the first species is thiosulfate.

14. A method according to claim 10 wherein the first solution contains sulfuric acid and iodide.

15. A method according to claim 14 wherein the sterilant comprises hydrogen peroxide and the test piece is peroxide resistant plastic or glass.

16. A method according to claim 14 wherein the first solution is prepared immediately prior to use by mixing a precursor solution comprising sulfuric acid with a precursor solution comprising iodide.

17. A method according to claim 10 wherein the sterilization regime comprises contacting the test piece with an aerosol of hydrogen peroxide in the sterilization space followed by removing the aerosol from the sterilization space.

18. A method according to claim 10 wherein the first species reactive with the sterilant is iodide and/or the second species reactive with the first species is thiosulfate.

19. A method according to claim 10 wherein the reaction between the first species and second species is monitored for a visual appearance at a predetermined time after mixing.

20. A method according to claim 10 wherein the first visual appearance is a yellow or brown color if the amount of residual sterilant exceeds the predetermined threshold.

21. A method according to claim 20 wherein the first visual appearance is caused by the presence of $I_2$ or $I_3^-$ and/or the second visual appearance is a colorless appearance if the amount of residual sterilant is below the predetermined threshold.

22. A method according to claim 10 wherein the method comprises removing the test piece from the sterilization regime.

* * * * *